(12) United States Patent
    Lacoste (10) Patent No.: US 10,058,526 B2
(45) Date of Patent: Aug. 28, 2018

(54) COMPOSITIONS CONTAINING PHEROMONES FOR TREATING BEHAVIOURAL OR MEDICAL PROBLEMS LINKED TO THE STRESS OF NON-HUMAN MAMMALS

(71) Applicant: CEVA SANTE ANIMALE, Libourne (FR)

(72) Inventor: Sandrine Lacoste, Carignan de Bordeaux (FR)

(73) Assignee: CEVA SANTE ANIMALE, Libourne (FR)

( * ) Notice: Subject to any disclaimer, the term of this patent is extended or adjusted under 35 U.S.C. 154(b) by 4 days.

(21) Appl. No.: 15/300,293

(22) PCT Filed: Mar. 31, 2015

(86) PCT No.: PCT/EP2015/057031
    § 371 (c)(1),
    (2) Date: Sep. 29, 2016

(87) PCT Pub. No.: WO2015/150386
    PCT Pub. Date: Oct. 8, 2015

(65) Prior Publication Data
    US 2017/0135976 A1    May 18, 2017

(30) Foreign Application Priority Data

Mar. 31, 2014 (EP) .................... 14162752

(51) Int. Cl.
    *A61K 31/225*    (2006.01)
    *A61K 31/20*    (2006.01)
(52) U.S. Cl.
    CPC ............ *A61K 31/225* (2013.01); *A61K 31/20* (2013.01)
(58) Field of Classification Search
    CPC .............................. A61K 31/225; A61K 31/20
    See application file for complete search history.

(56) References Cited

U.S. PATENT DOCUMENTS

| | | | | |
|---|---|---|---|---|
| 5,695,383 A | * | 12/1997 | Le Conte | A01K 47/04 449/2 |
| 6,077,867 A | * | 6/2000 | Pageat | A61K 31/20 514/558 |
| 2009/0224204 A1 | * | 9/2009 | Marion | C07C 67/22 252/364 |
| 2010/0292121 A1 | | 11/2010 | Jacquot et al. | |
| 2012/0052109 A1 | * | 3/2012 | Watkins | A01K 51/00 424/443 |

FOREIGN PATENT DOCUMENTS

| | | |
|---|---|---|
| WO | WO 2009/053347 | 4/2009 |
| WO | WO 2013/043879 | 3/2013 |
| WO | WO 2014/001836 | 1/2014 |

OTHER PUBLICATIONS

Vidal (http://www.rscspecialitychemicals.org.uk/docs/rsc-symposium/Sustainable-Solvents-Products-and-Process-Innovations_Thierry-Vidal_-RSC-Symposium-2012.pdf 2012).*
Anonymous, "FlexiSolv DBE esters" Jan. 30, 2013, retrieved from the Internet on May 8, 2014, URL:http://www.flexisolv.com/documents/FlexiSolv_DBE_esters_Technical_Data_Sheet. pdf, pp. 1-3, XP002724069.
Anonymous, "Rhodiasolv" Sep. 2003, retrieved from the Internet on May 8, 2014, URL:http://www.rhodia.com/en/binaries/Novecare_Rhodiasolv_brochure_2008_EN.pdf, pp. 1-6, XP-002724070.
Written Opinion in International Application No. PCT/EP2015/057031, dated Jun. 15, 2015, pp. 1-7.

* cited by examiner

*Primary Examiner* — Umamaheswari Ramachandran
(74) *Attorney, Agent, or Firm* — Saliwanchik, Lloyd & Eisenschenk (57) ABSTRACT

The invention relates to a composition containing pheromones comprising a carrier solvent, and to the use thereof for preventing and/or treating the behavioral or medical problems linked to the stress of non-human mammals. The invention also relates to a device for diffusing such a composition into the ambient air, and to a kit comprising said composition.

9 Claims, 3 Drawing Sheets

COMPOSITIONS CONTAINING PHEROMONES FOR TREATING BEHAVIOURAL OR MEDICAL PROBLEMS LINKED TO THE STRESS OF NON-HUMAN MAMMALS

CROSS-REFERENCE TO RELATED APPLICATION

This application is the U.S. national stage application of International Patent Application No. PCT/EP2015/057031, filed Mar. 31, 2015.

The present invention generally relates to the field of animal behavior and particularly pheromone compositions and methods for using these compositions to modify the behavior of non-human mammals. More particularly, the present invention relates to a pheromone-based composition comprising at least one carrier solvent and preferably a mixture of fatty acids and/or derivatives, preferably ester derivatives, in particular methyl esters, thereof. This pheromone-based composition is able to be administered to non-human mammals by diffusion into the ambient air, for the treatment of symptoms linked to stress or anxiety of said non-human mammals.

A pheromone is a chemical signalling compound or a mixture of substances produced naturally by numerous animals, especially non-human mammals, which elicits a predictable and specific behavioral response from another member of the same species.

Several types of pheromones, mainly in insects, have been identified, such as sex pheromones, trail pheromones, epideictic or spacing pheromones, recruitment pheromones, alarm pheromones, social regulation pheromones, etc.

A growing number of studies and marketed products tend to show the influence of pheromones, or compounds mimicking the action of pheromones, in the modification of the behavior of non-human animals, particularly mammals, such as canines, felines and/or equines.

Thus, patent application EP0724832 describes how the combination of valerian with a mixture of fatty acids, such as oleic acid, caproic acid, palmitic acid, azelaic acid, pimelic acid, 5-aminovaleric acid, n-butyric acid, α-methylbutyric acid, propionic acid, 5b-cholestan 3b-ol, p-hydroxyphenylacetic acid, and butyric acid, or ester derivatives, in particular methyl esters, thereof, prevents cats from urinating in a marked spot.

Patent application EP1047415 describes compositions for the treatment of stress, anxiety and/or aggressive behavior in a mammal, characterized by the mixing of at least three fatty acids: palmitic acid, linoleic acid and oleic acid, or derivatives thereof.

Patent application EP2515647 describes a pheromone composition making it possible to modify the behavior of an animal, comprising a mixture of at least 30% squalene, at least 10% linoleic acid and at least 1% 1-docosanol, the percentages being by weight, wherein the pheromone composition does not contain palmitic acid or oleic acid.

Patent application WO 2013/043879 describes a composition making it possible to modify the behavior of an animal, comprising an interomone which is more particularly described as being 2-methylbut-2-enal.

Finally, patent application EP2271204 describes a pheromone composition for appeasing dogs, referred to as pheromone "H", comprising linoleic acid, capric acid, pentadecylic acid, azelaic acid, pimelic acid, lauric acid, myristic acid, cholesterol, Cl-docosanol, squalene and BHT (butylhydroxytoluene).

These pheromone-based compositions customarily used to prevent or treat behavioral or medical problems linked to stress in non-human mammals are preferentially mixtures of fatty acids, or derivatives thereof, which are diffused into the ambient air from solid forms, emulsions or liquid forms.

These modes of administration have the aim of placing or distributing the pheromone composition in the animal's environment, either by incorporating the composition into an apparatus for diffusion, or by application, such as spraying via an aerosol or a spray, of the composition onto surfaces in the living environment of the animal.

The preferred mode of administration is the liquid form comprising at least one carrier solvent, so as to enable an application via, for example, a pump or by diffusion, using in particular electric diffusers.

Suitable carrier solvents are generally known in the art and are known to include organic liphophilic diluents, alcohols, ethylene glycol, propylene glycol, dipropylene glycol, ether, chloroform, benzene, carbon disulfide, oils, water or hydrocarbon-based solvents, in particular petroleum derivatives. For example, patent application WO 2013/043896 describes a pheromone composition dissolved in a suitable alcohol such as ethanol, propanol, isopropanol, butanol, pentanol, hexanol, heptanol, octanol or phenyethyl alcohol, to produce a liquid form capable of being sprayed by a pump or a spray.

Sprayable microemulsions are described in patent FR2795960 and are characterized in that they comprise fatty acids, preferably anionic or nonionic surfactants, and up to 30% co-surfactants such as linear or branched C1-C12 alcohols.

Unexpectedly, the applicant has highlighted novel carrier solvents which have notable advantages for administration, by diffusion into the ambient air, of pheromone-based compositions.

SUMMARY OF THE INVENTION

The present invention relates to a pheromone-based composition comprising at least one carrier solvent characterized by the following properties:
  a vapor pressure (VP) of between 1 and 10 Pa (measured at 20 or 25° C.), and
  a flash point of greater than or equal to 95° C.

Another object of the invention is a composition according to the invention, for a use in the prevention and/or treatment of at least one behavioral and/or medical problem linked to stress in a non-human mammal.

Another object of the invention is a diffusion device suited to diffusion of a composition according to the invention into the ambient air.

Another object of the invention is a kit comprising a composition and/or a device according to the invention and optionally instructions for use, intended to prevent and/or treat behavioral or medical problems linked to stress in non-human mammals.

DETAILED DESCRIPTION OF THE INVENTION

A first object of the invention relates to a pheromone-based composition comprising at least one carrier solvent characterized by the following properties:
- a vapor pressure (VP) of between 1 and 10 Pa (measured at 20 or 25° C.), and
- a flash point of greater than or equal to 95° C. (closed cup).

According to a preferred mode, the carrier solvent according to the invention is not a petroleum-derived solvent.

According to a preferred mode, the carrier solvent is a biodegradable synthetic product.

Preferentially, the carrier solvent of the pheromone-based composition according to the invention comprises at least one dibasic ester of formula (I):

This pheromone-based composition is able to prevent and/or treat at least one behavioral and/or medical problem linked to stress in a non-human mammal.

Pheromones

In the present invention, "pheromone-based composition" is intended to mean any composition comprising at least one substance secreted by the organism of a particular species which causes a predictable reaction in another individual of the same species or of another species. Said substance may be of natural or synthetic origin. Thus, more generally, said substance is at least one compound which mimics a substance secreted by the organism of a non-human mammal and is able to induce a change in behavior in a non-human mammal. Said substance may serve for example as a specific attractant, specific repellent, social communicator and/or sexual stimulant. Preferably, the pheromones are fatty acids or derivatives thereof. Thus, the pheromone-based composition preferably comprises at least one fatty acid or a derivative thereof, preferably an ester derivative, in particular methyl ester.

According to the invention, "fatty acids" is intended to mean saturated or unsaturated, linear or branched monocarboxylic and dicarboxylic acids with a hydrocarbon-based chain, able to prevent and/or treat behavioral or medical problems linked to stress in non-human mammals. These fatty acids are preferably C4-C22. They are especially chosen from propanoic (propionic) acid, butanoic (butyric) acid, pentanoic (valeric) acid, hexanoic (caproic) acid, heptanoic (enanthic) acid, octanoic (caprylic) acid, nonanoic (pelargonic) acid, decanoic (capric) acid, undecanoic (undecylic) acid, dodecanoic (lauric) acid, tridecanoic (tridecylic) acid, heptadecanoic (margaric) acid, octadecanoic (stearic) acid, eicosanoic acid, arachidonic acid, heneicosanoic (heneicosylic) acid, tricosanoic (tricosylic) acid, tetracosanoic (lignoceric) acid, pentacosanoic (pentacosylic) acid, hexacosanoic (cerotic) acid, heptacosanoic (heptacosylic) acid, octacosanoic (montanic) acid, nonacosanoic (nonacosylic) acid, triacontanoic (melissic) acid, henatriacontanoic (henatriacontylic) acid, dotriacontanoic (lacceroic) acid, tritriacontanoic (psyllic) acid, tetratriacontanoic (geddic) acid, pentatriacontanoic (ceroplastic) acid, hexatriacontanoic (hexatriacontylic) acid, nonanedioic (azelaic) acid, tetradecanoic (myristic) acid, pentadecylic (n-pentadecanoic) acid, and heptanedioic (pimelic) acid. Derivatives of these fatty acids, such as esters, in particular methyl esters, and/or salts, may also be used in the composition.

Derivatives of fatty acids is intended to mean all active, preferably volatile, derivatives, in particular more volatile than non-derivative fatty acids. Preferably, the derivatives are esterified forms, and more particularly methyl esters.

The compositions according to the invention may comprise any mixture of fatty acids and/or derivatives thereof liable to prevent and/or treat at least one behavioral or medical problem linked to stress in non-human mammals.

In one embodiment of the invention, the pheromones are fatty acids chosen from oleic acid, palmitic acid, n-butyric acid, linoleic acid, palmitoleic acid, capric acid, lauric acid, myristic acid, pentadecanoic acid, azelaic acid, pimelic acid, stearic acid, linolenic acid, pentanoic acid, arachidonic acid, isobutyric acid, pivalic acid, eicosapentaenoic acid, tridecanoic acid, docosahexaenoic acid, a derivative thereof and a mixture thereof.

Preferably, at least one of the fatty acids present in the pheromone-based composition according to the invention is linoleic acid, oleic acid or palmitic acid.

By way of examples of pheromones, without this being exhaustive, mention may be made of the following mixtures of fatty acids:
- a mixture of oleic acid and palmitic acid;
- a mixture of oleic acid and n-butyric acid;
- a mixture of oleic acid, palmitic acid and linoleic acid;
- a mixture of oleic acid, palmitic acid, linoleic acid and palmitoleic acid;
- a mixture of oleic acid, palmitic acid, azelaic acid and pimelic acid;
- a mixture of capric acid, lauric acid, myristic acid, palmitoleic acid, palmitic acid, linoleic acid and oleic acid;
- a mixture of oleic acid, palmitic acid, linoleic acid and myristic acid;
- a mixture of oleic acid, palmitic acid, linoleic acid, lauric acid and myristic acid;
- a mixture of oleic acid, palmitic acid, linoleic acid, myristic acid and pentadecanoic acid;
- a mixture of oleic acid, palmitic acid, linoleic acid, myristic acid, pentadecanoic acid and stearic acid;
- a mixture of oleic acid, palmitic acid, linoleic acid, myristic acid, lauric acid and pentadecanoic acid;
- a mixture of lauric acid, myristic acid, pentadecanoic acid, palmitic acid, stearic acid, oleic acid and linoleic acid; or
- a mixture of oleic acid, azelaic acid, pimelic acid and palmitic acid, or one of these mixtures in which at least one of the acids is replaced by one of the derivatives, preferably ester derivatives, in particular methyl esters, thereof.

The mixtures may comprise the above-mentioned fatty acids in suitable proportions known to those skilled in the art. By way of examples, the mixtures may comprise, relative to the total weight of the mixture:
- about 55 to 65% oleic acid, and 45 to 35% palmitic acid, or one of the respective derivatives thereof;
- about 45% oleic acid, 16% azelaic acid, 18% pimelic acid, and 21% palmitic acid, or one of the respective derivatives thereof;
- about 30% palmitic acid, 30% oleic acid, and 40% linoleic acid, or one of the respective derivatives thereof; or about 30% palmitic acid, 40% linoleic acid, 10% palmitoleic acid and 20% oleic acid, or one of the respective derivatives thereof.

In the pheromone-based compositions according to the invention, the fatty acids or derivatives thereof may be present in a proportion suited to diffusion into the ambient air. Preferably, a pheromone-based composition according to the invention comprises (pheromone fraction) between about 0.01 and about 5% fatty acids and/or derivatives thereof, preferably between about 0.05 and about 5%, preferably between about 2 and about 4%, preferably between about 3 and about 4%, in particular about 3.5%, relative to the total weight of the composition.

Unless indicated otherwise, the percentages are percentages by weight in the context of the present invention.

The term "about" relating to a value denotes the interval of between 10% more and less than said value.

Carrier Solvent

The carrier solvents in the composition according to the invention are solvents characterized by the following properties:
 a vapor pressure (VP) of between 1 and 10 Pa (measured at 20 or 25° C.), and
 a flash point of greater than or equal to 95° C. (closed cup).

The carrier solvent according to the invention has a vapor pressure (VP) of between 1 and 10 Pa (measured at 20 or 25° C.), preferably of between 4 and 8 Pa; it is advantageously between 5 and 7 Pa (such as 6.3 Pa).

The vapor pressure corresponds to that defined in the directive 1999/13/EC, Article 2, definition 17 on volatile organic compounds. It is therefore measured according to the conventional methods associated with this definition. More specifically, the carrier solvents according to the present invention are not volatile organic compounds (according to definition 17 of Article 2 of directive 1999/13/EC).

The carrier solvent according to the invention has a flash point of greater than or equal to 95° C., preferably between 96 and 200° C.; it is advantageously 98 or 144° C.

The closed cup flash point is generally measured by means of a Pensky-Martens apparatus. A semi-automatic apparatus of this type consists of a cup which may be filled with the liquid (generally a hydrocarbon) for which it is desired to know the flash point. The cup is then closed. The cover is provided with a thermometer, the tip of which is located above the liquid, in the vapors. The apparatus has a heater which makes it possible to raise the temperature degree by degree. Each time the temperature reaches one degree higher, a flame is lowered into the vapors. If ignition occurs, this means that the flash point has been reached; if not, the apparatus continues to increase the temperature of the liquid.

According to a preferred mode, the carrier solvent according to the invention is not a petroleum-derived solvent. In particular, the carrier solvent according to the invention is at least one solvent compound comprising, or consisting (optionally essentially) of, atoms of carbon, hydrogen and oxygen.

According to a preferred mode, the carrier solvent is a biodegradable synthetic product.

According to the invention, synthetic product is intended to mean a product that has been obtained by a partially, or preferably totally, synthetic process, and which does not exist in nature.

The term "petroleum-derived solvent" is intended to mean a solvent comprising only atoms of hydrogen and carbon.

According to the invention, the term "biodegradable synthetic product" is intended to mean a product which corresponds to OECD guideline no. 301 and/or 310.

In particular, a biodegradable product has a minimum degree of biodegradability of 60% obtained according to the tests described in standards AFNOR T90-312 and/or ISO7827, preferably of between 70 and 99%; advantageously it is 90%.

The carrier solvent is advantageously pure, that is to say that it has a degree of purity of greater than 95%.

The term "purity of greater than 95%" is intended to mean that the solvent does not comprise more than 5% by weight of impurities, that is to say of components other than those constituting the solvent, before it is placed in contact with the other components of the pheromone composition according to the invention. Preferably, the term "pure solvent" denotes a solvent comprising less than 5% of other compounds constituting the solvent, impurities and contaminants, more particularly less than 4%, less than 3%, less than 2% and even more preferentially less than 1% of other molecular species, impurities and contaminants.

The degree of purity may be evaluated by any analytical method known to those skilled in the art, such as high performance liquid chromatography (HPLC), gas chromatography (GC), mass spectrometry or nuclear magnetic resonance. These analytical methods may, of course, be coupled or combined with one another.

The solvent used in the present invention is advantageously not classified as dangerous by inhalation.

The term "not classified as dangerous by inhalation" is intended to mean a solvent which does not carry any of the following risk phrases: R20: Harmful by inhalation, R23: Toxic by inhalation, and R26: Very toxic by inhalation. The risk phrases are defined in Annex III of European Directive 67/548/EEC, supplemented by Directive 2001/59/EC.

Preferably, the carrier solvent does not contain any C8 to C18 carbon-based monoester. Advantageously, the carrier solvent is an odorless solvent.

The term "odorless" denotes a compound from which no odor can be perceived by the human user when the pheromone-based composition is diffused, preferably into the ambient air.

Advantageously, the carrier solvent has at least one of the properties identified above and advantageously all these properties.

As examples of carrier solvents according to the invention, mention may especially be made of dibasic esters, isosorbide dimethyl ether, isononyl isononanoate and propylene carbonate. Propylene carbonate or advantageously dibasic esters are preferred.

Dibasic Esters

The dibasic esters according to the invention are compounds of formula (I)

in which $R_1$, $R_2$ and $R_3$ are independently linear or branched alkyl groups comprising from 1 to 10 carbon atoms.

An "alkyl" group according to the invention is a saturated linear or branched hydrocarbon-based group comprising from 1 to 10 carbon atoms.

The alkyl group preferably comprises from 1 to 4 carbon atoms. The alkyl group may especially be chosen from methyl, ethyl, n-propyl, isopropyl, n-butyl, isobutyl and tert-butyl groups. In particular, the alkyl group is a methyl, ethyl, n-propyl, n-butyl or isobutyl group.

In one embodiment, the $R_1$ and $R_3$ groups are identical. $R_1$ and $R_3$ are preferably two isobutyl groups.

In one embodiment, $R_2$ is chosen from ethyl, n-propyl, n-butyl and isobutyl groups.

As examples of dibasic esters, mention may especially be made of dimethyl esters such as dimethyl 2-methylpentanedioate and diisobutyl esters such as diisobutyl hexanedioate, diisobutyl glutarate and diisobutyl succinate, and mixtures thereof.

These dibasic esters are in particular used as solvents in the present invention.

As examples of solvents comprising at least one dibasic ester, mention may especially be made of the solvents of the RHODIASOLV range, sold by Solvay, for example RHODIASOLV IRIS (dimethyl 2-methylpentanedioate) or RHODIASOLV DIB (diisobutyl hexanedioate, diisobutyl glutarate and diisobutyl succinate), and also the mixtures thereof in any proportions.

Preferably, the solvent comprising at least one dibasic ester is a mixture of diisobutyl hexanedioate, diisobutyl glutarate and diisobutyl succinate (such as in the product RHODIASOLV DIB).

In the compositions according to the invention, the carrier solvent, and in particular the dibasic ester(s), may be present in any proportion suited to diffusion into the ambient air. Preferably, a composition according to the invention comprises between about 50 and about 99.9% carrier solvent, and in particular dibasic ester(s), preferably between about 75 and about 99.5%, preferably between about 90 and about 99%, preferably between about 95 and about 97%, in particular about 96.5%, expressed as percentage by weight relative to the total weight of the composition.

Other Components

The compositions according to the invention may optionally contain other compounds in addition to those which have been described above, in particular in addition to the fatty acids and dibasic esters as defined above.

These additional compounds, well known to those skilled in the art, may be especially solvents, propellants, fragrances, attractant compounds, fatty alcohols, steroids, antioxidants and/or terpenes.

The solvents may be organic lipophilic diluents, alcohols, ethylene glycol, propylene glycol, dipropylene glycol, ether, chloroform, benzene, carbon disulfide, oils, including nonvolatile and unstable liquids and oils, or water. Mention may also be made, as other solvents, of C8-C10 triglycerides, decanol, triethyl citrate, glycofurol (tetraethylene glycol), neopentanoic acid, isononanoic acid, and esters thereof, such as isodecyl neopentanoate, octyl isononanoate, esters of isopropanol, myristic acid, citric acid or sebacic acid, such as isopropyl myristate or diisopropyl sebacate.

The propellants may be chlorofluorocarbons (CFCs) such as trichloromonofluoromethane, dichlorodifluoromethane, dichlorotetrafluoroethane and hydrochlorofluorocarbons (HCFCs) or hydrofluorocarbons (HFCs) such as chlorodifluoromethane, trifluoromonofluoroethane, chlorodifluoroethane, difluoroethane, and heptafluoropropane, hydrocarbons such as propane, butane, isobutene, and compressed gases such as nitrogen, carbon dioxide and nitrous oxide.

The fragrances may be floral essences, citrus plant flowers, oils, conifer extracts or spices.

The attractant compounds are essential oils, such as valerian or catnip oil.

A fatty alcohol is for example 1-docosanol, a steroid may be cholesterol, an antioxidant may be a lipophilic antioxidant such as BHT (butylhydroxytoluene) and a terpene could be squalene.

Those skilled in the art are able to adjust the nature and quantity of each additional compound in the composition according to the invention as a function of the desired characteristics for the pheromone composition.

Behavioral or Medical Problems Linked to Stress in Non-Human Mammals

It is accepted that stress may generate numerous medical or behavioral problems in non-human mammals. The commonly accepted sources of stress and/or fear in non-human mammals comprise, for example, arrival in a new place, weaning, separation from the mother with a view to adoption and/or changing place, transport (especially motorized vehicles), boredom, lack of exercise, anxiety linked to separation, loud noises, overpopulation, events which cause the animal to, for example, bark, jump or beg, and also anxiety linked to the presence of new people or new mammals, or else anxiety linked to visits to the veterinarian and any other non-routine event in the life of the non-human mammal.

Non-human mammals which are stressed following exposure to such events or conditions will generally exhibit behavioral symptoms and/or develop highly undesirable medical problems linked to stress. Undesirable behaviors are generally recognized and the most frequently encountered are urine marking, aggressiveness, scratching, excessive grooming, territorial conflicts, reduced play and social contact, hyperagitation or prostration and destruction. The medical problems linked to stress and/or fear are generally recognized and the most frequently encountered are cystitis, dermatological problems, especially excessive licking, alopecia, anorexia, obesity, diarrhea and respiratory infections.

Non-Human Mammals

The term "non-human mammals" is intended to mean domestic, farm or zoo mammals, and more particularly felines, canines and equines.

Modes of Administration

The effectiveness of the composition according to the invention may be obtained, for example, by administration into the environment of non-human mammals by virtue, for example, of spraying an aerosol or spray comprising the composition, or even by diffusion of the composition into the ambient air via a liquid diffuser. In all cases, the composition is sufficiently volatile for the animal to inhale it and therefore to be exposed to a sufficient quantity of the composition to produce a notable behavioral effect. For example, a reduction in undesirable external behavior may be readily verifiable, such as the notable reduction of aggressiveness, scratching, barking and/or jumping, and may be supplemented by the observation of other physical indicators of stress, such as heart rate, weight changes, and the secretion of stress hormones, such as cortisol.

The composition according to the invention may also be used to prevent the appearance of undesirable behaviors. In this case, the composition of the present invention may be used to induce a temporary state of reduced activity, or a reduction in excitability in order to allow the non-human mammal to better withstand the stress to come, such as fireworks, being moved or the arrival of another animal.

The non-human mammal will be exposed to the composition of the invention by any method enabling the inhalation thereof over a sufficient period of time to observe a modification of the behavior of the target, as determined according to observations of the behavior. Typically, depending on the route of administration chosen and the situation generating the stress, the non-human mammal will be exposed to the composition of the invention over a period of at least one second to several months, but in all cases for any period of time necessary to obtain a satisfactory behavioral effect. For example, an animal suffering from temporarily-induced anxiety, such as fireworks, may require exposure to the composition of the invention before, during and/or after the anxiety-producing event, to relieve anxiety and the associated behavior(s). On the other hand, an animal exposed to a stressing stimulus over a longer, continuous period, such as an animal exposed to a new pet in the home, may benefit from regular exposure to the composition of the invention over a prolonged period.

The preferential mode of administration of the composition of the invention is diffusion into the ambient air, which is more particularly carried out by means of an electric diffuser.

One object of the invention is a device for diffusion into the ambient air, suited to diffusion of a pheromone-based composition according to the invention into the ambient air.

In one embodiment, the diffusion device is a diffuser, in particular an electric diffuser.

Preferably, the diffuser is a liquid refill diffuser, that is to say that it is used with a liquid refill. The liquid refill contains a composition according to the invention as defined above.

The diffuser is preferably suited to diffusion of the composition according to the invention for a duration of at least one month (about 30 days).

The diffuser, preferably the electric diffuser, according to the invention makes it possible to preferably obtain a temperature of the element for heating the pheromone-based compositions which is strictly less than 130° C., especially less than or equal to 120° C., in particular less than or equal to 100° C.

The heating elements are well-known to those skilled in the art and are, for example applied to diffuse volatile substances, as described in patent EP1714662.

Another object of the invention is a kit comprising a pheromone-based composition according to the invention and/or a device according to the invention, and optionally instructions for use, intended to prevent and/or treat behavioral or medical problems linked to stress in non-human mammals.

A final object of the invention is a method for diffusing a composition according to the invention, comprising the diffusion of said composition into the ambient air. The diffusion method preferably comprises the use of a device or a kit according to the invention. The diffusion is preferably carried out by heating, in particular according to the temperatures specified above.

Advantages of the compositions, devices, kits and methods according to the invention The pheromone compositions according to the invention have a significantly reduced diffusion variability compared to compositions comprising hydrocarbon-based carrier solvents, especially compared to compositions of fatty acids for which the only carrier solvents are C14-C19 hydrocarbon-based petroleum-derived solvents.

In addition, the use of solvents such as those defined in the present invention, especially dibasic esters, makes it possible to greatly reduce the electric power of the diffuser and the temperature of the heating element required for diffusion of the compositions of fatty acids. Thus, the compositions according to the present invention may be diffused with diffusers characterized by powers of less than or equal to 5.6 W, and more particularly by powers of less than 3 W.

Similarly, the compositions according to the present invention may be diffused at heating element temperatures of less than 130° C., especially less than or equal to 120° C., in particular less than or equal to 100° C. The reduction in the power and temperature of the heating elements consequently makes it possible to reduce the heating-up temperature of the device, thereby reducing any burnt odor and thus reducing the perceived risks of burns for the user.

The examples below are given solely by way of nonlimiting illustration of the invention.

EXAMPLES

Example 1: Diffusion of Pheromone Compositions According to the Invention 48 ml of solvent to be tested are placed in a 5.6 W electric diffuser. The amount of solvent diffused is measured for 30 days following plugging in of the diffuser, and the average diffusion of product per day is calculated and summarized in Table 1 below:

TABLE 1

| Solvent | Diffusion of product (g/day) |
| --- | --- |
| Control (Solvent derived from petroleum distillate) | 2 |
| Isopropyl myristate | 1 |
| Diisopropyl sebacate | 1 |
| Isononyl isononanoate | 2 |
| Glycofurol | 0.5 |
| Triethyl citrate | 1 |
| Dibasic ester | 4 |
| Propylene carbonate | 4 |
| Isosorbide dimethyl ether | 2 |

Example 2: Variation in Diffusion for a Pheromone-Based Composition Comprising a Dibasic Ester Solvent The diffusion ability of various solvents was evaluated as a function of the power of the diffuser and the temperature of the heating elements of the diffuser.

The conditions are summarized in Table 2 below. The results are presented in the graph of FIG. 1.

TABLE 2

| Solvent | Control (Solvent derived from petroleum distillate) | RHODIASOLV IRIS | RHODIASOLV DIB |
| --- | --- | --- | --- |
| Power | 5.6 W | 4.2 W | 4.2 W |
| Temperature | 130° C. | 100° C. | 100° C. |

The solvents have the following composition:

Solvent derived from petroleum distillate is a hydrocarbon-based solvent derived from a petroleum distillate in hydrotreated medium.

RHODIASOLV IRIS (sold and marketed by Solvay): dimethyl 2-methylpentanedioate.

RHODIASOLV DIB (sold and marketed by Solvay): diisobutyl hexanedioate, diisobutyl glutarate and diisobutyl succinate.

Figure 1:
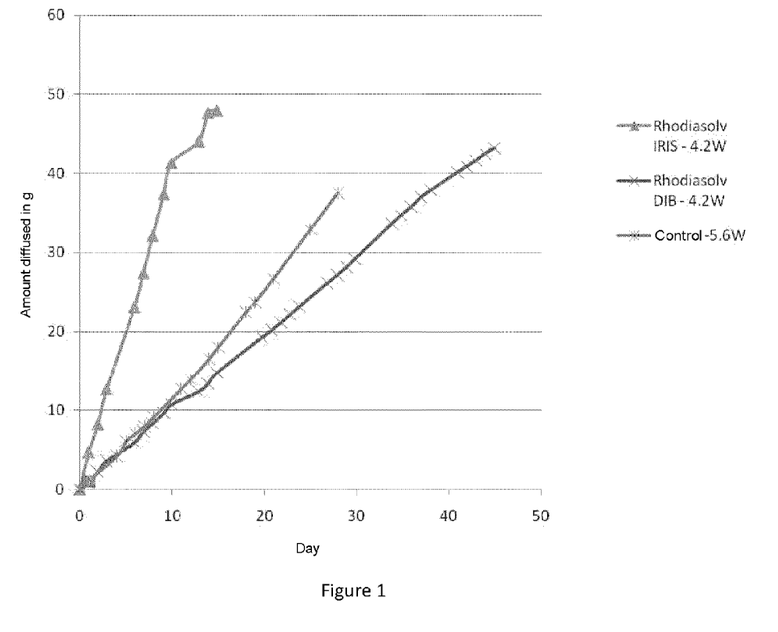
FIG. 1: Variation in the diffusion of various solvents depending on time.

The graph of FIG. 1 illustrates that the diffusion of dibasic ester solvents at a lower temperature of the heating element and lower powers of the diffuser is comparable to that observed under standard conditions for a diffuser of volatile compounds (solvent derived from petroleum distillate at 130° C. with a power of 5.6 W).

Example 3: Study of the Coefficient of Variation of a Composition According to the Invention The coefficient of variation (CV) of a composition according to the invention comprising 3.5% active agents, 19.3% RHODIASOLV DIB and 77.2% RHODIASOLV IRIS by volume on 3 2.8 W diffusers was studied each day for 10 days (Table 3). By way of comparison, the coefficient of variation of a composition comprising 3.5% active agents and a solvent derived from petroleum distillate as the only solvent, obtained on 6 5.6 W diffusers, is given (Table 4). The active agents correspond to the mixture of esters of fatty acids described in composition 4 of Example 5.

TABLE 3

| Days | 1 | 2 | 3 | 6 | 10 |
|---|---|---|---|---|---|
| Average amount diffused per day (g) | 2.017 | 2.012 | 2.10 | 1.67 | 1.59 |
| CV (%) | 4.85 | 2.61 | 0.84 | 6.345 | 3.08 |

TABLE 4

| Days | 1 | 2 | 3 | 6 | 10 |
|---|---|---|---|---|---|
| Average amount diffused per day (g) | 1.73 | 1.64 | 1.58 | 1.7 | 1.47 |
| CV (%) | 11.1 | 19.2 | 20.7 | 20.8 | 17.7 |

The coefficients of variation are clearly lower for the composition according to the invention, even using only 3 2.8 W diffusers, than those obtained for the composition comprising a solvent derived from petroleum distillate.

Example 4: Study of the Diffusion Obtained at Different Diffuser Powers

Figure 2:
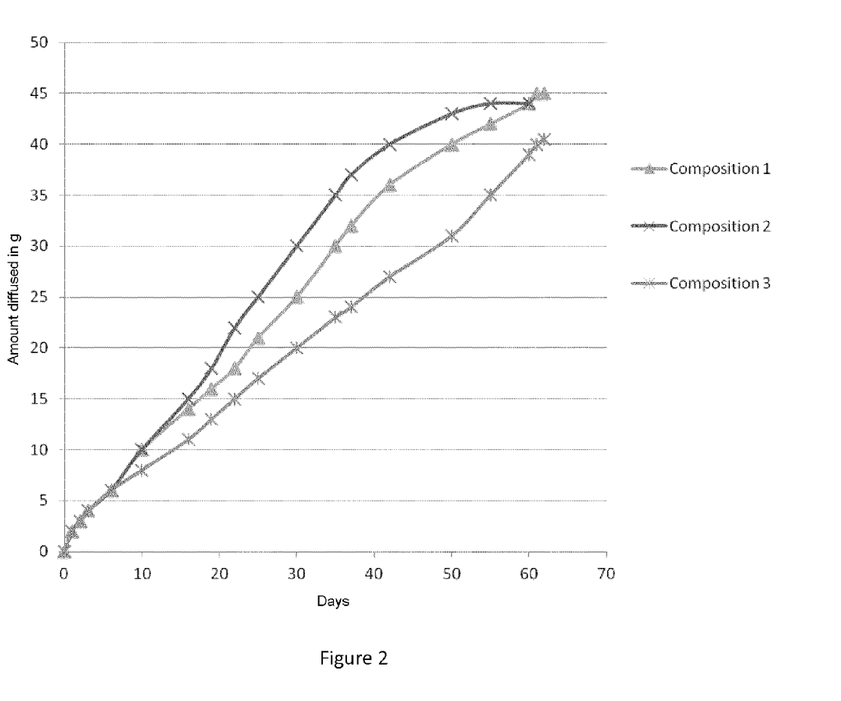
FIG. 2: Diffusion of compositions according to the invention at a power of 2.8 W.
Figure 3:
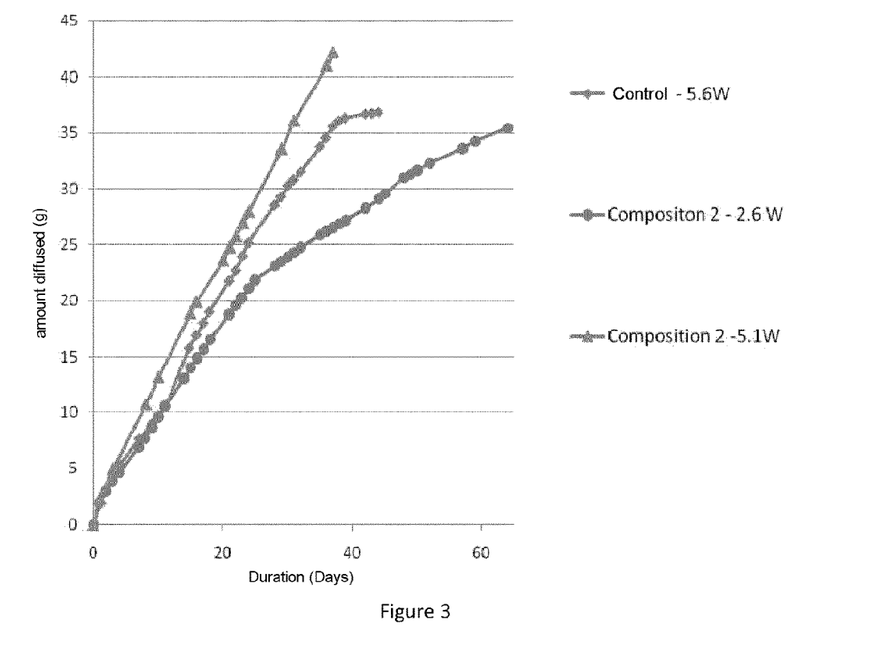
FIG. 3: Diffusion of a composition according to the invention at various powers, and comparison with a control composition diffused at 5.6 W.

The loss of weight obtained as a function of time of compositions according to the invention at a power of 2.8 W is represented in FIG. 2. The compositions are as follows (% by volume):
Composition 1: 3.5% active agents, 48.25% RHODIASOLV DIB, 48.25% RHODIASOLV IRIS;
Composition 2: 3.5% active agents, 19.3% RHODIASOLV DIB, 77.2% RHODIASOLV IRIS; and
Composition 3: 3.5% active agents, 28.95% RHODIASOLV DIB, 67.55% RHODIASOLV IRIS.
The active agents correspond to the mixture of esters of fatty acids described in composition 4 of Example 5.
The graphs of FIG. 2 show that very good diffusion can be obtained using a power of only 2.8 W.
Similarly, FIG. 3 gives the diffusion curves obtained for composition 2 according to the invention at 2.6 W and 5.1 W, and also the diffusion curve obtained for a composition comprising a solvent derived from petroleum distillate as the solvent, at 5.6 W (control: 5.6 W). The diffusions obtained for the compositions according to the invention at 2.6 W and 5.1 W are comparable to those obtained with a solvent derived from petroleum distillate at 5.6 W. Consequently, it is possible, using the compositions according to the invention, to obtain diffusion equivalent to that observed with a 5.6 W diffuser with lower power and hence lower energy expenditure.

Example 5: Compositions According to the Invention

| Composition 4 | in grams |
|---|---|
| Mixture of esters of fatty acids comprising: Linoleic acid Oleic acid Stearic acid Palmitic acid Pentadecanoic acid Myristic acid Lauric acid | 3.5 |
| RHODIASOLV DIB | q.s. 100 ml |

Figure 4:
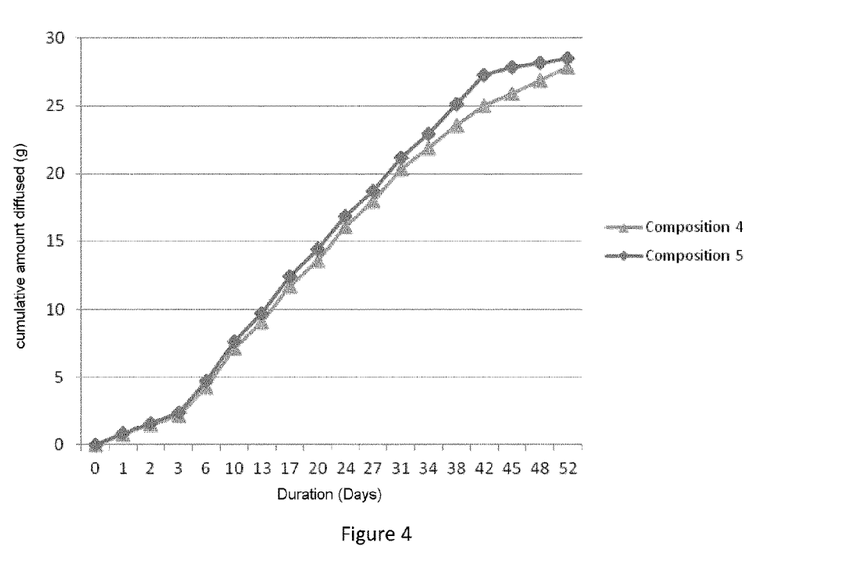
FIG. 4: Stability of the diffusion profile of a composition according to the invention over two (2) months.

Example 6: Stability of the Diffusion Profile of a Composition According to the Invention Over Two (2) Months Diffusion, by a diffuser of a power of 3 W, of the composition according to Example 5 (composition 4) was compared to that of a composition comprising the same ingredients and having been stored for 14 months at 25° C. and 60% residual humidity (composition 5).
The results are presented in FIG. 4.
The graphs clearly demonstrate that the properties of diffusion and evaporation of the composition according to the invention are preserved over time. This composition is therefore storage-stable.

The invention claimed is:
1. A pheromone-based composition comprising at least one pheromone and at least one carrier solvent selected from the group consisting of dimethyl 2-methylpentanedioate, diisobutyl hexanedioate, diisobutyl glutarate, diisobutyl succinate, and at least one mixture thereof and wherein the pheromone of said composition comprises at least one fatty acid selected from the group consisting of oleic acid, palmitic acid, n-butyric acid, linoleic acid, palmitoleic acid, capric acid, lauric acid, myristic acid, pentadecanoic acid, stearic acid, azelaic acid, pimelic acid, linolenic acid, pentanoic acid, arachidonic acid, isobutyric acid, pivalic acid, eicosapentaenoic acid, tridecanoic acid, docosahexaenoic acid, an ester derivative thereof and a mixture thereof, said composition being storage-stable for at least two months and allowing for diffusion of the at least one pheromone.
2. The composition as claimed in claim 1, wherein the composition comprises between 50 and 99.9% of carrier solvent by weight relative to the total weight of the composition.
3. The composition as claimed in claim 1, wherein the carrier solvent comprises between 95% and 97% by weight relative to the total weight of the composition.
4. The composition as claimed in claim 1, wherein the carrier solvent comprises about 96.5% by weight relative to the total weight of the composition.
5. The composition as claimed in claim 1, wherein said composition comprises 0.01% to about 5% by weight of fatty acid or a derivative thereof, relative to the total weight of the composition.

6. A method for treating at least one behavioural or medical problem linked to stress in a non-human animal comprising administering a composition as defined in claim 1 to said non-human animal.

7. The method as claimed in claim 6, wherein the behavioral problem linked to stress is selected from the group consisting of urine marking, aggressiveness, scratching, excessive grooming, territorial conflicts, reduced play and social contact, hyperagitation, prostration, and destruction.

8. The method as claimed in claim 6, wherein the medical problem linked to stress is selected from the group consisting of cystitis, dermatological problems, alopecia, anorexia, obesity, diarrhea, and respiratory infections.

9. A kit comprising a composition as claimed in claim 1 and/or a device suited to diffusion of said composition into the ambient air and optionally instructions for use.

* * * * *